US 6,576,773 B2

(12) United States Patent
Nakahara et al.

(10) Patent No.: US 6,576,773 B2
(45) Date of Patent: Jun. 10, 2003

(54) METHOD FOR PRODUCTION OF PYROMELLITIC DIANHYDRIDE

(75) Inventors: Kenji Nakahara, Himeji (JP); Tsukasa Takahashi, Himeji (JP); Shigetaka Takamiya, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 10/142,136

(22) Filed: May 9, 2002

(65) Prior Publication Data

US 2002/0169330 A1 Nov. 14, 2002

(30) Foreign Application Priority Data

May 10, 2001 (JP) ........................................ 2001-140455

(51) Int. Cl.⁷ ............................................. C07D 493/00
(52) U.S. Cl. ...................................................... 549/239
(58) Field of Search ......................................... 549/239

(56) References Cited

U.S. PATENT DOCUMENTS

| 3,328,428 A | 6/1967 | McMahon |
| 4,598,157 A | 7/1986 | Scharf |
| 4,725,291 A | 2/1988 | Ueoka et al. |

FOREIGN PATENT DOCUMENTS

| JP | 07278153 | 10/1995 |
| JP | 10265474 | 10/1998 |

*Primary Examiner*—Samuel Barts
*Assistant Examiner*—Sikarl A. Witherspoon
(74) *Attorney, Agent, or Firm*—Selitto, Behr & Kim

(57) ABSTRACT

A method for producing crystals of pyromellitic dianhydride is disclosed which is characterized by setting the water content of an atmosphere used in handling the crystals of pyromellitic dianhydride at a temperature of not higher than 120° C. at a level of not more than 4 vol. %. Particularly by supplying an inert gas having a water content of not more than 4 vol. % to the step of production, it is made possible to prevent the conversion of pyromellitic dianhydride by hydration very efficiently.

6 Claims, 2 Drawing Sheets

METHOD FOR PRODUCTION OF PYROMELLITIC DIANHYDRIDE

BACKGROUND OF THE INVENTION

1. Field of the Invention

This invention relates to a method for the production of a pyromellitic dianhydride which is prevented from being hydrated and more particularly to a method for the production of pyromellitic dianhydride, characterized by the fact that while pyromellitic dianhydride formed by cooling a pyromellitic dianhydride-containing gas is in the process of being collected, pulverized, and stored, the water content in an atmosphere accommodating the produced pyromellitic dianhydride is set at a level of not more than 4 vol. % when the temperature of the atmosphere is not higher than 120° C.

2. Description of the Related Art

Pyromellitic dianhydride is a subliming substance and is mainly useful as a raw material for such heat-resisting polymers as polyimide resin or as a hardening agent for epoxy resin. The methods which are available for the production of such pyromellitic dianhydride in high purity come under the two types, namely those of the type resorting to the gas phase oxidation and those of the type resorting to the liquid phase oxidation.

The methods of liquid phase oxidation enjoy the advantage of manifesting a high selectivity and nevertheless suffer from the disadvantage of inferior productivity because they are implemented in a batch process. The methods of liquid phase oxidation produce pyromellitic acid and, therefore, require this product to be converted by the removal of the elements of water and necessitate a drying step at an elevated temperature, a subliming and recrystallizing step, or a step for the removal of the elements of water involving use of a large volume of acetic anhydride. Since these methods possibly give rise to such heavy metals and halogenides as originate in the catalysts used in the relevant reaction solutions, they further necessitate a step for separating and recovering such impurities from the respective products or a step for disposing waste liquid emanating from the plant.

Another known method produces pyromellitic dianhydride by subjecting such a tetraalkylbenzene as 1,2,4,5-tetraethyl benzene or 1,2,4,5-tetramethyl benzene to catalytic gas phase oxidation with a molecular oxygen-containing gas. The method of gas phase oxidation permits continuous production of pyromellitic dianhydride. Particularly, this method forms the pyromellitic dianhydride in the reaction gas owing to the catalytic gas phase oxidation and therefore obviates the necessity for depriving the product of the elements of water. The method of gas phase oxidation, therefore, is at an advantage in directly obtaining pyromellitic dianhydride of high purity by being implemented in combination with gas phase collection utilizing reverse sublimation.

Generally, the methods which are available for recovering in the form of crystals the pyromellitic dianhydride which has been collected by the technique of reverse sublimation are known in the three types, those of the type using the procedure which comprises separating a pyromellitic dianhydride-containing gas in a cooling layer furnished with fine holes and raking the crystals by rotating teeth of the shape of a comb or brush; those of the type using the procedure which comprises introducing a pyromellitic dianhydride-containing gas as accompanied by wear-resistant particles into a cooling device and peeling resultantly separated crystals by collision of the particles; those of the type using the procedure which comprises inflicting a mechanical shock as with an air knocker on a cooling device thereby peeling the crystals from the cooling surface; and those of the type using the procedure which comprises elevating the temperature of the wall face having deposited thereon crystals of pyromellitic dianhydride to a level higher than the subliming temperature of pyromellitic dianhydride under the operating pressure inside a collecting device thereby removing the adhering crystals by sublimation and causing the remainder of grown crystals to detach themselves from the wall face and fall down.

The official gazette of JP-A-10-265,474 discloses a method for recovering pyromellitic dianhydride by introducing a pyromellitic dianhydride-containing gas into a vertical recovering column provided with a crystal deposition surface, causing the gas to deposit pyromellitic dianhydride in the form of crystals on the crystal deposition surface and elevating the temperature of the crystal deposition surface to a level in the range of 210~260° C. thereby causing the crystals to peel and fall from the crystal deposition surface.

After the grown crystals of pyromellitic dianhydride have undergone such steps as peeling, exfoliating, and pulverizing, the practice of recovering the pulverized crystals and stowing the recovered pulverized crystals in such a container as the bag for storage is generally followed. As a technique for producing pyromellitic dianhydride by utilizing reverse sublimation, the official gazette of JP-A-07-278,153 discloses a method which effects collection of pyromellitic dianhydride by subjecting tetraalkylbenzene to catalytic gas phase oxidation and cooling the gas thereby inducing precipitation of crystals of pyromellitic dianhydride. The official gazette discloses a method for the production of pyromellitic dianhydride which comprises a series of such steps as cooling a pyromellitic dianhydride-containing gas obtained by the catalytic gas phase oxidation of tetraalkylbenzene with a heat exchanger to about 250₂0 C., then transferring the cooled gas to a pre-cooler, cooling it therein to a temperature in the range of 150~200° C., and withdrawing the precipitate through an extracting line and meanwhile cooling and collecting the residual gas in a subsequent main collecting device.

The crystals obtained freshly from the collecting device are too hot to be handled as a finished product. Thus, the practice of recovering such crystals, cooling and pulverizing them, and then packing the cooled and pulverized crystals for shipment is generally followed. In the case of obtaining a pyromellitic dianhydride-containing gas by the reaction of catalytic gas phase oxidation and cooling and collecting the crystals of pyromellitic dianhydride, the reaction gas contains the water by-produced by the reaction of catalytic gas phase oxidation. In concert with this cooling of the reaction gas, the water reacts with pyromellitic dianhydride and this reaction induces conversion of pyromellitic dianhydride into pyromellitic monoanhydride (PMMA) and pyromellitic acid (PMA) by hydration. These products produced by the addition of the elements of water are impurities in the target product and form a cause for degrading the purity of the product. For the purpose of preventing the pyromellitic dianhydride from yielding to ring scission, the practice of adjusting the cooling in the main collecting device so as to keep the temperature from falling below 110° C. has prevailed heretofore (the official gazette of JP-A-07-278,153). The reason for this adjustment is that since the reaction of catalytic gas phase oxidation suffers the reaction gas to contain a water component without fail, the water component is inevitably condensed and precipitated in consequence of the fall of the temperature to a level below the dew point of water. Since this method prohibits the fall of the temperature below 110° C., however, it is deficient in efficiency of cooling and production is substantially in need of a plurality of collecting devices including the main collecting device.

The aim of provisionally hydrating the crystals and then reverting them by the elimination of the elements of water, however, is at a disadvantage in necessitating initial investment, requiring incorporation of a separate step, and raising the price of the product.

SUMMARY OF THE INVENTION

The present inventors made an elaborate study about the relation between the ratio of the conversion of pyromellitic dianhydride crystal by hydration and the water content of the atmosphere. They have consequently found that the amount of pyromellitic acid (PMA) to be formed abruptly increases when the water content in the atmosphere exceeds 4 vol. %, whereas the hydration of the pyromellitic dianhydride can be prevented even under the temperature condition of not higher than 120° C. when the water content in the atmosphere is not more than 4 vol. %. This invention has been perfected as a result.

According to this invention, pyromellitic dianhydride can be produced while preventing it from being hydrated. In this case, the hydration can be prevented efficiently by introducing an inert gas having a water content of not more than 4 vol. % into the atmosphere enveloping the crystals of pyromellitic dianhydride till the atmosphere is displaced with the inert gas.

DETAILED DESCRIPTION OF THE PREFERRED EMBODIMENTS

This invention concerns a method for the production of pyromellitic dianhydride, characterized by setting the water content of the atmosphere used in handling crystals of pyromellitic dianhydride at a temperature of not higher than 120° C. at a level of not more than 4 vol. %. Since pyromellitic dianhydride possesses high reactivity with water, it reacts with the steam in the air and readily converts to PMMA and PMA. This invention, in the light of the relation between the water content of the atmosphere enveloping crystals of pyromellitic dianhydride and the conversion by hydration, contemplates substantially preventing the conversion into PMMA and PMA by setting the water content of the atmosphere at a level of not more than 4 vol. %. The method of this invention is useful when the crystals of pyromellitic dianhydride mentioned herein are those crystals of pyromellitic dianhydride that are precipitated by subjecting to reverse sublimation the pyromellitic dianhydride-containing gas obtained by catalytic gas phase oxidation of tetraalkylbenzene. This assertion will be explained in detail below.

Figure 1:
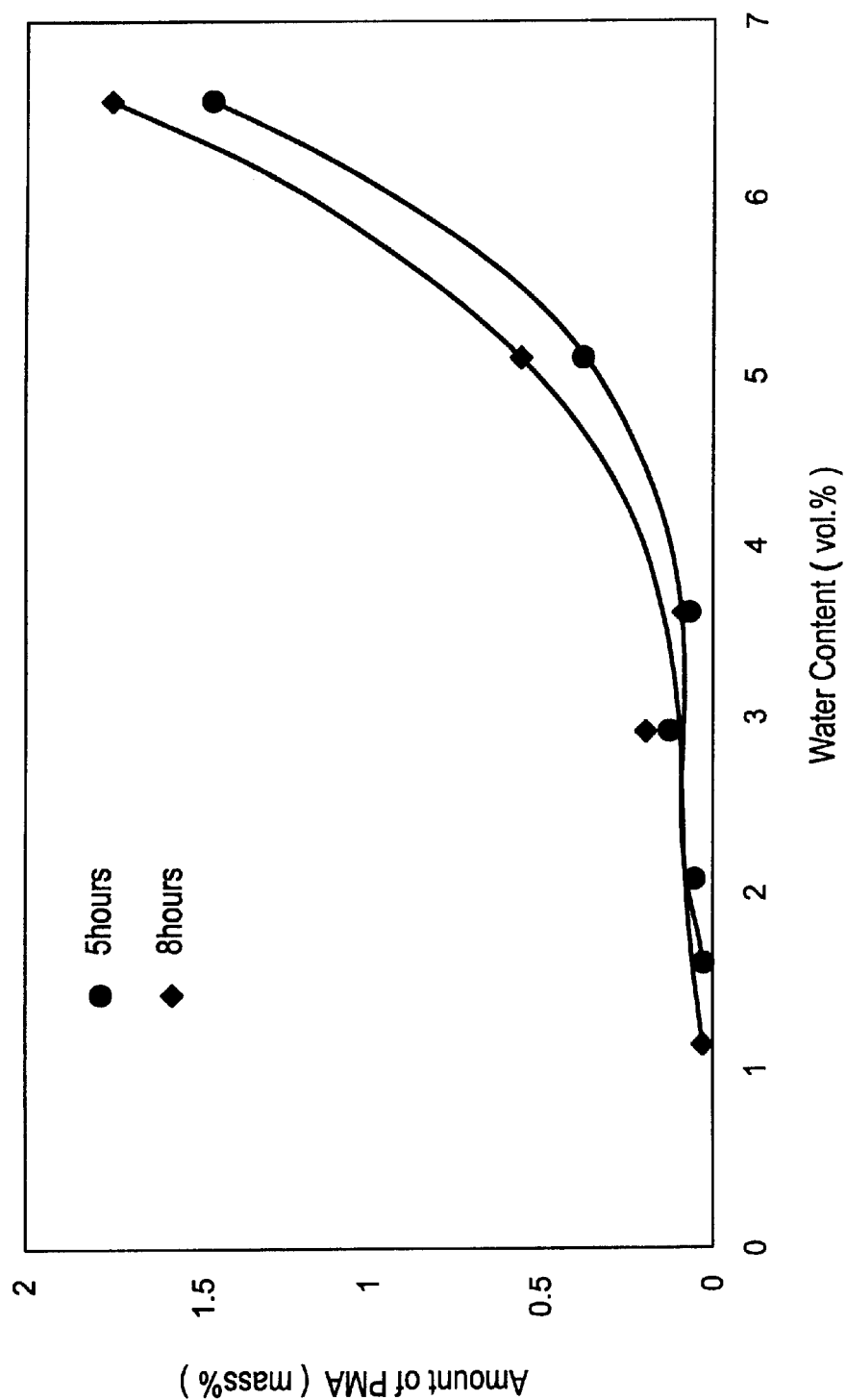
FIG. 1 shows the results of the determination of the amount of pyromellitic acid (PMA) formed in the atmosphere of a varying water content at a temperature of 30° C. after the elapse of 5 hours and 8 hours in a thermo-hygrostat.

In the conventional production of pyromellitic dianhydride by catalytic gas phase oxidation, the relation between the temperature and the water content of the atmosphere enveloping crystals at the step for cooling a pyromellitic dianhydride-containing gas and collecting the crystals formed by the cooling and at the subsequent step for pulverizing the crystals has not received due recognition and the relation between the temperature and the water content at each of the component steps has not been elucidated. Specifically, the reaction of catalytic gas phase oxidation of tetraalkylbenzene by-produces water and suffers the water component contained in the raw material gas supplied to the reactor to persist. When the pyromellitic dianhydride-containing gas obtained by the reaction of catalytic gas phase oxidation is cooled to induce precipitation of the crystals thereof, however, no substantial conversion by hydration occurs so long as the temperature of the atmosphere enveloping the crystals of pyromellitic dianhydride exceeds 120° C., i.e. a level greatly surpassing the dew point of water. If this temperature is not higher than 120° C., however, the water component contained in the atmosphere will possibly cause conversion of pyromellitic dianhydride by hydration. Thus, the official gazette of JP-A-07-278,153, for example, defines the temperature to be not lower than 110° C. This limit has formed a cause for degradation of the productivity. An elaborate study of the relation between the water content of the atmosphere enveloping pyromellitic dianhydride and the conversion of pyromellitic dianhydride by hydration, however, has elucidated the fact that is depicted in FIG. 1. FIG. 1 shows the results of the determination of the amount of pyromellitic acid formed by allowing pyromellitic dianhydride to stand at rest for durations of 5 hours and 8 hours in the atmosphere of a thermo-hygrostat having the temperature adjusted at 30° C. and the water content adjusted at varying levels in the range of 0~7 vol. %. As shown in FIG. 1, the amounts of pyromellitic acid formed after the elapse of 5 hours and 8 hours were confined to such very low values as not exceeding 0.2 mass % when the water content was limited to not more than 4 vol. %. This fact means that by adjusting the water content to not more than 4 vol. %, it is made possible to lower the speed at which pyromellitic dianhydride absorbs moisture to the extent of very effectively preventing the conversion of pyromellitic dianhydride by hydration. This invention is based on this discovery.

The method for the production of pyromellitic dianhydride according to this invention, therefore, is characterized by setting the water content at not more than 4 vol. % in the atmosphere used in handling such crystals as are produced by cooling a pyromellitic dianhydride-containing gas till precipitation of crystals of pyromellitic dianhydride at temperatures of not higher than 120° C. The method of this invention for the production of pyromellitic dianhydride can be used particularly favorably in producing pyromellitic dianhydride by utilizing the reaction of catalytic gas phase oxidation. Now, a preferred embodiment of this invention will be described below with reference to FIG. 2.

Figure 2:
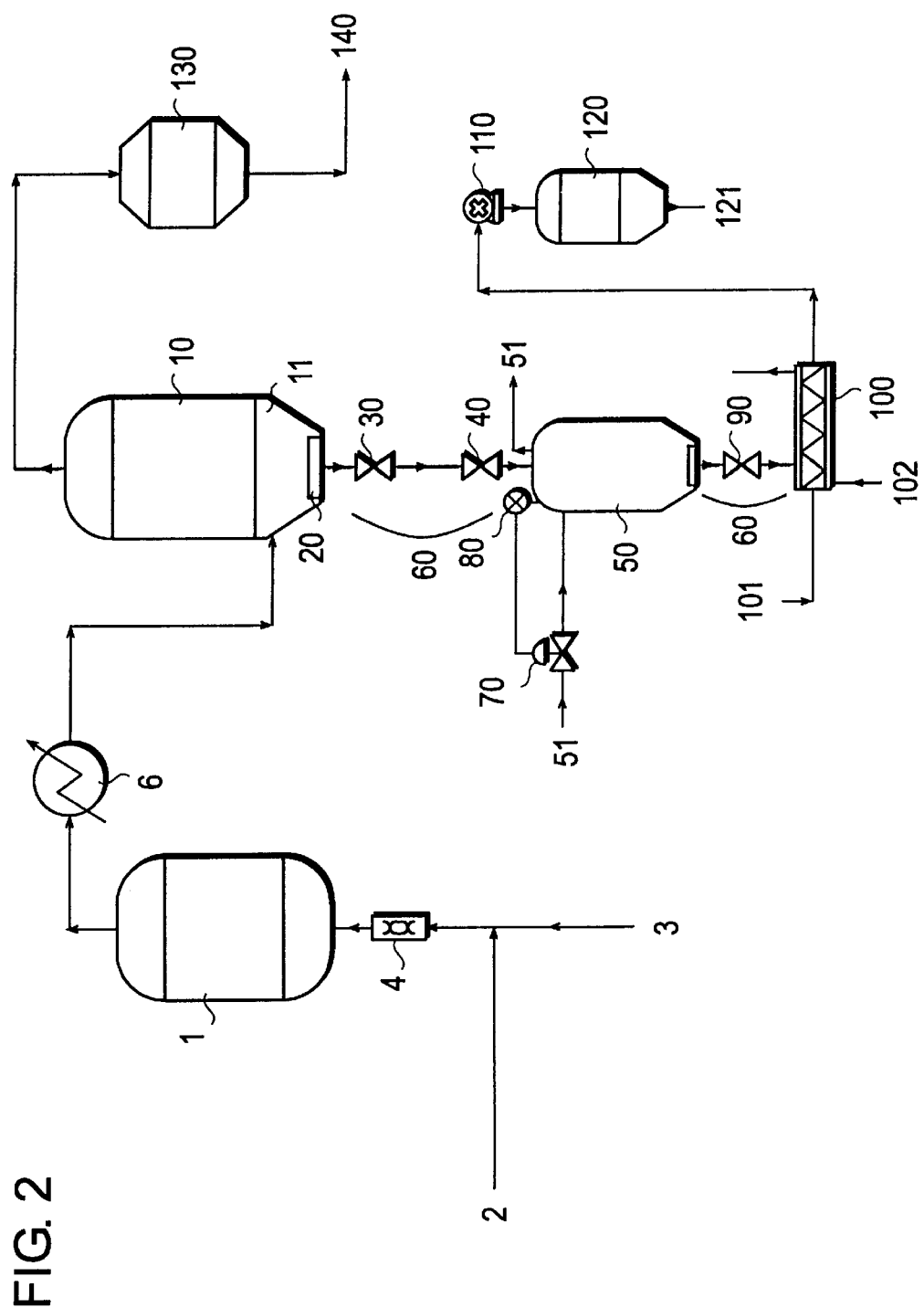
FIG. 2 is a flow diagram depicting a preferred embodiment of the method of this invention for the production of pyromellitic dianhydride.

For a start, the raw material gas prepared by mixing tetraalkylbenzene 2 and a molecular oxygen-containing gas 3 in a mixer 4 is supplied to a reactor 1 packed in advance with an oxidizing catalyst and a pyromellitic dianhydride-containing gas is obtained through an outlet port of the reactor as illustrated in FIG. 2. Since the gas so obtained has an elevated temperature, it is cooled through heat recovery by the use of a heat exchanger 6 to the extent falling short of inducing precipitation of pyromellitic dianhydride and subsequently the cooled gas is introduced into a lower conical section 11 of a collecting device 10. In the collecting device 10, the gas is subjected to reverse sublimation at a temperature not higher than the temperature for precipitation of pyromellitic dianhydride and higher than 120° C. to induce precipitation of crystals of pyromellitic dianhydride. The crystals of pyromellitic dianhydride precipitated herein are accumulated in the lower conical section 11 of the collecting device at a temperature not higher than the temperature for the precipitation of pyromellitic dianhydride and higher than 120° C.

Then, the crystals are discharged through the bottom part of the lower conical section 11 of the collecting device 10 into a crystal receiving vessel 50 through the medium of a discharging device 20 such as the circle feeder. Though this discharging device does not need to be limited to the circle feeder, it is preferred to be in such a type as permits direct application of an external force to the crystals. The crystal receiving vessel 50 is so constructed as to be isolated from the ambience lest the pyromellitic dianhydride-containing gas should flow into the crystal receiving vessel 50 during the discharge of the crystals from the collecting device 10 into the crystal receiving vessel 50. In the process for the discharge of the crystals to the crystal receiving vessel 50, when the discharging device 20 itself is devoid of the function of isolating the collecting device 10 from the ambience, a crystal transferring part 60 is interposed between the crystal receiving vessel 50 and the discharging device 20 and this crystal transferring part 60 is separately provided with such blocking devices such as the valves 30 and 40 with the aim of preventing the crystal receiving vessel 50 from admitting the atmospheric gas in the collecting device 10, the ambient air, and extraneous matter. As concrete examples of the other blocking device, a shut-off valve, a rotary valve, and a double bumper may be cited.

An inert gas 51 having a water content of not more than 4 vol. % is introduced into the crystal receiving vessel 50. In this case, the inert gas 51 is supplied for this introduction while the pressure thereof is adjusted by means of a pressure controlling valve 70 and a pressure gauge 80 for the purpose of causing the internal pressure of the crystal receiving vessel 50 to be higher than the internal pressure of the collecting device 10 and consequently preventing the atmospheric gas in the collecting device 10 from flowing into the crystal receiving vessel 50.

Since the crystals, which have been accumulated in the crystal receiving vessel 50, have an elevated temperature, they must be cooled before they are obtained as a finished product. Thus, the crystals are transferred from the lower part of the crystal receiving vessel 50 to a cooling device 100 and are cooled by the cooling device 100 after the parts connected to the collecting part 10 have been blocked by closing the valve 30 or 40. As concrete examples of the cooling device 100, a screw feeder and a steam belt may be cited. Since any of these cooling devices is invariably handled in the atmosphere of an inert gas having a water content of not more than 4 vol. %, it is constructed to avoid inflow of the ambient air and to introduce into the cooling device 100 an inert gas 101 having a water content of not more than 4 vol. %.

Further, where the particle diameter of the component crystals of the product is to be controlled, the cooled crystals are introduced into a classifier and crusher. Then, the pulverized crystals are accumulated in a product hopper 120 and the crystals of pyromellitic dianhydride, which are a product 121 are withdrawn through the lower part of the product hopper 120 and packed for shipment. The crusher 110 is so constructed that the interior thereof may not admit inflow of the ambient air and may be filled with an inert gas having a water content of not more than 4 vol. % with a view to preventing the crystals from succumbing to conversion by hydration at the pulverizing step. Besides, the product hopper 120 for accumulating the pulverized crystals has the water content therein lowered by introducing therein an inert gas having a water content of not more than 4 vol. %.

To be specific, the pyromellitic dianhydride is preferred to be produced as follows.

The production of the pyromellitic dianhydride by catalytic gas phase oxidation is accomplished by subjecting 1,2,4,5-tetramethylbenzene or 1,2,4,5-tetraethylbenzene as a tetra-alkylbenzene to catalytic gas phase oxidation with a molecular oxygen-containing gas in the presence of a vanadium pentoxide-containing catalyst. The catalyst to be used in this case may be selected from among the known catalysts intended for the production of pyromellitic dianhydride such as, for example, a catalyst which contains vanadium and silver as essential components and has an atomic ratio of silver to vanadium in the range of 0.001~0.2 as disclosed in the official gazette of JP-A-07-171,393 and a vanadium-molybdenum-tungsten type oxidizing catalyst disclosed in the official gazette of JP-A-08-41,067.

The reaction of catalytic gas phase oxidation is preferred to be performed in the reactor keeping the catalyst heated to a temperature in the range of 240~460° C. and handling the raw material gas prepared by mixing 10~60 g of the tetraalkylbenzene with 1 $m^3$ of the molecular oxygen-containing gas (normal state). From the reactor 1, the reaction product gas containing pyromellitic dianhydride is discharged.

The molecular oxygen-containing gas 3 which is supplied to the reactor 1 in this case is allowed to contain such inert gases as carbon dioxide and nitrogen besides oxygen. The use of air as the molecular oxygen-containing gas 3 proves convenient.

The reaction gas which remains after precipitating the crystals of pyromellitic dianhydride contains the by-produced water and the water component entrained by the molecular oxygen-containing gas. By supplying an inert gas having a water content of not more than 4 vol. % and making it displace the reaction gas, it is made possible to adjust the water content of the atmospheric gas during the course of retaining the temperature of the reaction gas at a level of not higher than 120° C. without reference to the water content of the molecular oxygen-containing gas.

The course of handling the atmosphere encompassing the crystals at temperatures of not higher than 120° C. in this invention does not need to be limited to the steps illustrated in FIG. 2 but may embrace such component steps of the known process for the production of pyromellitic dianhydride such as the transfer part from the collecting device to the crystal receiving vessel, the crystal receiving vessel, the transfer part from the crystal receiving vessel to the cooling device, the cooling operation in the cooling device, the transferring operation from the cooling device to the crusher, the pulverizing operation in the crusher, the transferring operation from the crusher to the product hopper, and the step for packing the product. When the temperature of the atmosphere enveloping the crystals is kept at a level of not higher than 120° C. and the water content in the atmosphere is kept at a level of not more than 4 vol. % throughout the course from the collecting device through the step for filling the product, this invention proves to be more effective.

This invention can be aimed at the pyromellitic dianhydride-containing gas that is obtained by the reaction of catalytic gas phase oxidation of a tetraalkylbenzene. Since this reaction of catalytic gas phase oxidation is an exothermic reaction, the pyromellitic dianhydride-containing gas which is discharged from the reactor generally has a temperature in the range of 300~550° C. Then, the pyromellitic dianhydride-containing gas is introduced into the collecting device 10 in order that it may be subjected to reverse sublimation for the purpose of permitting collection of pyromellitic dianhydride.

In the collecting device 10, the pyromellitic dianhydride-containing gas is cooled to a temperature exceeding 120° C. and not exceeding 200° C., preferably falling in the range of 150~190° C. and enabled to precipitate crystals thereof through reverse sublimation. If this temperature falls short of 120° C., the shortage will be at a disadvantage in suffering the crystals to undergo conversion by hydration. Conversely, if the temperature exceeds 200° C., the excess will be at a disadvantage in lowering the ratio of recovery of the crystals of pyromellitic dianhydride.

For the purpose of adjusting the temperature of the pyromellitic dianhydride-containing gas at a level exceeding 120° C. and not exceeding 200° C., the method which effects the adjustment of the temperature in the range mentioned above by supplying other cooling gas to the collecting device 10 and the method which accomplishes the cooling by providing the collecting device 10 in the outer periphery thereof with an external cylinder for circulating a coolant and circulating a coolant kept at a temperature in the range of 150~190° C. are usable.

The term "reverse sublimation" as used in this invention refers to the act of collecting in a solid state the pyromellitic dianhydride that exists in a gaseous state. The collection of the pyromellitic dianhydride through the reverse sublimation, therefore, does not need to be limited to the method mentioned above but may be attained by any method which is only required to be capable of recovering the pyromellitic dianhydride in a solid state. Further, the shape of the collecting device 10, the kind of the cooling device, the method for pressing the gas, and the method for cooling the gas are irrelevant. The methods which are available for collecting pyromellitic dianhydride by subjecting a pyromellitic dianhydride-containing gas to reverse sublimation include a method which comprises cooling a pyromellitic dianhydride-containing gas formed by the catalytic gas phase oxidation of a tetraalkylbenzene with a preheater to a temperature of not higher than 200° C. thereby inducing precipitation of part of crystals of pyromellitic dianhydride and thereafter, by the use of a main collecting device having a metallic net or movable chain stretched or suspended, precipitating the pyromellitic dianhydride from the gas in a supersaturated state as disclosed in the official gazette of JP-A-07-278,153; a method which comprises retaining the difference between the dew point of pyromellitic dianhydride and the temperature of the cooling medium at a magnitude of not more than 60° C. and setting the average linear velocity of a pyromellitic dianhydride-containing gas at a level in the range of 0.05~0.5 m/sec during the course of the heat-exchange effected between the pyromellitic dianhydride-containing gas and the cooling medium through a heat transfer wall as disclosed in the official gazette of JP-A-08-59,668; a method which comprises introducing a subliming substance-containing gas into a vertical recovering device thereby inducing precipitation of the subliming substance on a crystal deposition surface in the recovering device and subsequently lowering the temperature of the crystal deposition surface to a level lower than the temperature existing during the deposition of crystals thereby recovering the crystals by peeling and falling as disclosed in the official gazette of JP-A-10-279,522; and a method which comprises introducing a pyromellitic dianhydride-containing gas into a vertical recovering device thereby causing the pyromellitic dianhydride to be deposited in the form of crystals on a crystal deposition surface in the recovering device and subsequently heating the crystal deposition surface to a temperature in the range of 210~260° C. thereby peeling the crystals from the crystal deposition surface and recovering the separated crystals as disclosed in the official gazette of JP-A-10-265,474, for example. It should be noted, however, that the temperature for the deposition of the crystals by the reverse sublimation of the pyromellitic dianhydride-containing gas should be in the range of not lower than 120° C. and not higher than 200° C.

Then, the crystals are withdrawn from the collecting device 10 and transferred to the crystal receiving vessel 50 for temporary storage. Since the temperature in the collecting device 10 exceeds 120° C. in this case, the problem of suffering the pyromellitic dianhydride to succumb to conversion by hydration due to the contact with the ambient air will not arise. The step that follows the treatment in the collecting device 10, however, has the possibility of incurring conversion by the addition of the elements of water because the temperature at times falls below 120° C. For the purpose of preventing the interior of the crystal receiving vessel 50 from admitting inflow of water component to the fullest possible extent, therefore, the production apparatus ought to be prevented from admitting inflow of the ambient air through the joints used therein and the collecting device 10 as well ought to isolate the atmosphere from the ambience.

To be specific, a blocking means such as, for example, the valves 30 and 40, is interposed between the collecting device 10 and the crystal receiving vessel 50. First, with the valve 30 in an opened state and the valve 40 in a closed state, the crystals in the collecting device 10 is supplied by the discharging device 20 such as a circle feeder to the intervening space between the valves 30 and 40 which are provided in the crystal transferring part 60. Then, the valve 30 is closed and the valve 40 is opened to transfer the crystals to the crystal receiving vessel 50. In this case, the crystals are supplied till they fill to capacity the space between the valves 30 and 40 in the crystal transferring part 60. By controlling the valves 30 and 40 as described above, it is made possible to minimize the amount of the atmospheric gas from the collecting device 10 and decrease the amount of the atmospheric gas from the collecting device 10 suffered to enter the crystal receiving vessel 50 as well.

Then, an inert gas having a water content of not more than 4 vol. is supplied to the crystal receiving vessel 50 so as to adjust the water content of the atmosphere in the crystal receiving vessel 50 to a level of not more than 4 vol. %. The reason for using the inert gas in this manner is that the conversion of the pyromellitic dianhydride by hydration can be prevented even when the temperature falls below 120° C. As concrete examples of the inert gas 51 which can be directly used, carbon dioxide and nitrogen gas which are commercially available. The exhaust gas having a water content of not more than 4 vol. % which has been recovered from other production process may be used instead. This inert gas 51, while being supplied to the crystal receiving vessel 50, has the pressure thereof adjusted by means of a pressure control valve 70 or a pressure gauge 80 so that the internal pressure of the crystal receiving vessel 50 may rise above the internal pressure of the collecting device 10 and the gas in the collecting device 10 may be prevented from flowing into the crystal receiving vessel 50.

When the crystals in the crystal receiving vessel 50 are transferred to the cooling device 100 like a screw feeder and cooled therein, the valve 40 is closed and the valve 90 interposed between the crystal receiving vessel 50 and the cooling device 100 is opened to effect the transfer of the crystals to the cooling device 100. Then, the valve 90 is closed lest the ambient air other than the inert gas should flow into the crystal receiving vessel 50. By supplying the inert gas 101 having a water content of not more than 4 vol. % to the cooling device 100 and establishing a closed system from the cooling device 100 through the crusher 110 and further through the product hopper 120, therefore, it is made possible to adjust the atmosphere enveloping the crystals of pyromellitic dianhydride to a water content of not more than 4 vol. % at a temperature of not higher than 120° C. owing merely to the supply of the inert gas to the cooling device 100. For this cooling in the cooling device 100, such methods as introduction of a cooling water 102 and introduction of a cooling gas to the jacket.

This invention, owing to the method described above, is capable of producing pyromellitic dianhydride while preventing this pyromellitic dianhydride from succumbing to conversion by hydration. This method of production permits the residual reaction gas to emanate from the upper part of the collecting device 10. The emanating gas contains such organic substances as trimellitic acid, maleic acid, citraconic acid, and 4-methylphthalic acid, which are by-produced by the reaction of catalytic gas phase oxidation, and carbon monoxide and carbon dioxide. The noxious carbon monoxide is also present in the exhaust gas which occurs after the recovery of pyromellitic dianhydride and a bad odor is given off. These could be suffered to exert a heavy load on the ecological system including human bodies. These organic substances are fine particulates in shape. When they are recovered as with a bag filer, for example, they readily clog the filter and degrade the efficiency of treatment. It is, therefore, preferable to have the exhaust gas containing such fine organic substances disposed by the treatment of catalytic waste gas combustion so that the highly noxious carbon monoxide may be converted into carbon dioxide.

More specifically, the disposal of the exhaust gas remaining after the collection of the pyromellitic dianhydride by the treatment of waste gas combustion may be implemented by the treatment of catalytic waste gas combustion and the method of direct combustion, for example. This invention particularly prefers this disposal to be effected by the treatment of catalytic waste gas combustion. The method of direct combustion requires the gas containing the target component to be maintained at a high temperature exceeding the ignition temperature of the component and, therefore, entails the problem of increasing the cost of fuel. In contrast, the treatment of the catalytic waste gas combustion has a lower treating temperature. Depending on the concentration of the component contained, the disposal may be fulfilled solely by application of heat during the startup of the treating device and this device may be so designed as to obviate completely the cost of fuel during the regular operation and lower the running cost as well. In the flow diagram of FIG. 2, for example, the exhaust gas flowing from the collecting device 10 is transferred to a device 130 for the catalytic waste gas combustion and a waste gas 140 is discharged from the device.

The catalyst to be used in this treatment of the catalytic waste gas combustion may be selected from among known combustion catalysts such as the catalysts which oxidize a given exhaust gas on the surface of catalyst with the oxygen in the air and as the noble metal type catalysts having platinum, palladium, or rhodium deposited thereon. Such a combustion catalyst is preferable because it is capable of enabling organic substances contained in the exhaust gas from the production of pyromellitic dianhydride to be thoroughly combusted by the reaction of oxidation at a low temperature. Incidentally, this catalyst is allowed to assume the shape of granules, honeycombs, or ribbons, depending on the shape of the carrier serving to support such an active substance as noble metal. The shape of the catalyst is not limited to the shapes mentioned above. The use of the catalyst of the shape of honeycombs proves particularly advantageous among other shapes because this catalyst suffers from only small pressure loss and, therefore, permits the reactor to be designed in a compact construction. By the use of this combustion catalyst, the disposal can be carried out at a low temperature.

The disposal by the catalytic waste gas combustion may be specifically materialized by a method which comprises preparing a cylinder provided with an inlet port and an outlet port for a waste gas and furnished therein with a bed of a catalyst of the shape of honeycombs and introducing a given exhaust gas into the cylinder. The hydrocarbons contained in the waste gas are thoroughly oxidized on the catalyst and subsequently converted into harmless and odorless carbon dioxide and water and discharged.

In this invention, the exhaust gas to be introduced into the device 130 for the catalytic waste gas combustion has the amount thereof so adjusted that the temperature of the catalyst bed may fall in the range of 200~600° C., preferably in the range of 300~500° C., and particularly preferably in the range of 300~400° C., with a view to controlling the amount of heat generated by the treatment of the catalytic waste gas combustion. For the adjustment of this amount of supply, a method which consists in controlling the flow rate of the exhaust gas supplied to the treatment of the catalytic waste gas combustion and a method which consists in mixing the exhaust gas with other molecular oxygen-containing gas may be used.

This invention prefers the exhaust gas remaining after the collection of pyromellitic dianhydride to be adjusted to a temperature of not lower than 200° C. before it is disposed by the waste gas combustion. The catalytic activity manifested by the disposal of the catalytic waste gas combustion is variable with the temperature of the gas to be supplied. Thus, the disposal by the combustion can be expedited by having the temperature of the exhaust gas adjusted in advance to a level of not lower than 200° C. Particularly, the catalyst which is used in the disposal by the aforementioned catalytic waste gas combustion can accomplish the disposal by combustion fully satisfactorily because it excels in the activity of combustion at low temperatures.

EXPERIMENTS

Now, this invention will be described more specifically below with reference to working examples thereof.

Example 1

Pyromellitic dianhydride was produced by the use of an apparatus constructed as shown in FIG. 2.

First, a reactor 1 furnished with a stainless steel reaction tube measuring 25.4 mm in inside diameter and packed with a catalyst in the shape of pellets 5 mm in diameter and 5 mm in length which was formed mainly of vanadium pentoxide and titanium dioxide was prepared. A raw material gas formed by mixing 30 g of 1,2,4,5-tetramethylbenzene with 1 $m^3$ of air (normal state) was introduced into the reactor 1 and subjected to catalytic gas phase oxidation under the conditions of 5000 $h^{-1}$ in space velocity and 385° C. in reaction temperature to afford a pyromellitic dianhydride-containing gas.

The pyromellitic dianhydride-containing gas thus obtained was introduced into the lower part of the collecting device 10 and subjected to reverse sublimation at a temperature of 170° C. to induce precipitation of crystals of pyromellitic dianhydride. The temperature of the lower part of the collecting device 10 was 180° C. When the catalyst precipitated in the lower part of the collecting device 10 were analyzed, they were found to contain 0.04 mass % of pyromellitic acid resulting from the conversion of pyromellitic dianhydride by hydration and 0.002 mass % of pyromellitic monoanhydride.

Then, the crystals consequently accumulated were transferred to the crystal receiving vessel 50 by means of a circle feeder (discharging device 20) disposed in the lower part of the collecting device 10. The crystal transferring part 60 and the valves 30, 40, and 90 were severally disposed between the circle feeder and the crystal receiving vessel 50 and between the crystal receiving vessel 50 and the jacketed screw conveyor (cooling device 100).

The pressure of the crystal receiving vessel 50 was adjusted by the use of the pressure controlling valve 70 so as to surpass the pressure in the lower part of the collecting device 10 by a margin of not less than 1000 Pa. The inert gas having a water content of 1.0 vol. % was introduced therein. On this occasion, the valve 30 was opened with the valve 40 kept in a closed state and the circle feeder was set operating to discharge the crystals which had accumulated in the lower part of the collecting device 10. The discharged crystals were accumulated temporarily in the crystal transferring part and, after setting the valve 30 in a closed state and the valve 40 in an opened state, the crystals were discharged into the crystal receiving vessel 50. Then, by closing the valve 40 and opening the valve 90, the crystals were forwarded into the jacketed screw conveyor (cooling device 100).

By causing the cooling water 102 at a temperature of about 30° C. to flow into the jacket of the cooling device 100, the crystals were cooled to the neighborhood of 35° C. and meanwhile fed to the crusher 110. For the purpose of preventing the water component in the gas phase to succumb to condensation during the cooling step and the pulverizing step and during the zone of transfer therebetween, the inert gas 101 having the water content thereof adjusted to a level of not more than 1.0 vol. % was forwarded at a rate of 0.5 m³ (normal state)/h.

When the finished product obtained after the pulverization was analyzed, it was found to contain 0.06 mass % of pyromellitic acid and 0.004 mass % of pyromellitic monoanhydride.

Example 2

The procedure of Example 1 was faithfully repeated, excepting the water content of the inert gas forwarded to the crystal receiving vessel 50, the cooling device 100, the crusher 110, and the transferring parts was changed to 4 vol. %. When the finished product obtained after the pulverization was analyzed, it was found to contain 0.1 mass % of pyromellitic acid and 0.05 mass % of pyromellitic monoanhydride.

Control

The procedure of Example 1 was faithfully repeated, excepting the water content of the inert gas forwarded to the crystal receiving vessel 50, the cooling device 100, the crusher 110, and the transferring parts was changed to 5.0 vol. %. When the finished product obtained after the pulverization was analyzed, it was found to contain 1.2 mass % of pyromellitic acid and 0.2 mass % of pyromellitic monoanhydride.

The entire disclosure of Japanese Patent Application No. 2001-140,455 filed on May 10, 2001, including specification, claims, drawings and summary are incorporated herein by reference in its entirety.

What is claimed is:

1. A method for producing crystals of pyromellitic dianhydride which comprises adjusting the water content of a gaseous atmosphere surrounding the produced crystals of pyromellitic dianhydride to be not more than 4 vol. % when the temperature of the gaseous atmosphere is not more than 120° C.

2. A method according to claim 1, wherein the crystals have been precipitated from a pyromellitic dianhydride-containing gas by the technique of reverse sublimation.

3. A method according to claim 1, wherein the water content of the gaseous atmosphere is adjusted by introducing an inert gas having a water content of not more than 4 vol. % to the gaseous atmosphere.

4. A method according to claim 2, wherein the pyromellitic dianhydride-containing gas is prepared by catalytic gas phase oxidation of a tetraalkylbenzene with a molecular oxygen-containing gas.

5. A method according to claim 4, wherein the tetraalkylbenzene is selected from the group consisting of 1, 2, 4, 5-tetramethyl-benzene and 1, 2, 4, 5-tetraethylbenzene.

6. A method for producing crystals of pyromellitic dianhydride by cooling a pyromellitic dianhydride-containing gas obtained by catalytic gas phase oxidation thereby inducing precipitation of the crystals of pyromellitic dianhydride, which comprises adjusting the water content of a gaseous atmosphere surrounding the crystals of pyromellitic dianhydride to be not more than 4 vol. %, when the temperature of the gaseous atmosphere is not more than 120° C.

* * * * *